United States Patent
Mayer et al.

(10) Patent No.: US 6,690,569 B1
(45) Date of Patent: Feb. 10, 2004

(54) CAPACITIVE SENSOR

(75) Inventors: Felix Mayer, Zürich (CH); Moritz Lechner, Zürich (CH)

(73) Assignee: Sensirion A/G, Zurich (CH)

( * ) Notice: Subject to any disclaimer, the term of this patent is extended or adjusted under 35 U.S.C. 154(b) by 0 days.

(21) Appl. No.: 10/130,969
(22) PCT Filed: Sep. 6, 2000
(86) PCT No.: PCT/IB00/01261
 § 371 (c)(1),
 (2), (4) Date: Sep. 3, 2002
(87) PCT Pub. No.: WO01/42776
 PCT Pub. Date: Jun. 14, 2001

(30) Foreign Application Priority Data

Dec. 8, 1999 (CH) .............................. 2251/99

(51) Int. Cl.⁷ .............................. H01G 4/005
(52) U.S. Cl. ...................... 361/303; 361/305; 361/281; 361/283.1; 361/283.4; 361/286
(58) Field of Search ................. 361/303, 286, 361/322, 302, 305, 277, 280, 283.1, 283.4, 281, 287, 329, 278, 283.3

(56) References Cited

U.S. PATENT DOCUMENTS

| | | | |
|---|---|---|---|
| 4,347,550 A | 8/1982 | Rockliff | 361/286 |
| 4,429,343 A | 1/1984 | Freud | 361/286 |
| 4,564,882 A | 1/1986 | Baxter et al. | 361/286 |
| 5,707,148 A | * 1/1998 | Visser et al. | |
| 5,719,740 A | 2/1998 | Hayashi et al. | 361/283.4 |
| 5,837,886 A | * 11/1998 | Nakahara et al. | |
| 5,840,255 A | * 11/1998 | Kappel et al. | |
| 5,989,398 A | * 11/1999 | Young et al. | |
| 6,191,593 B1 | 2/2001 | Tartagni et al. | 324/687 |
| 6,252,759 B1 | 6/2001 | Lange et al. | 361/283.1 |
| 6,265,222 B1 | * 7/2001 | DiMeo, Jr. et al. | |
| 6,326,228 B1 | * 12/2001 | Hughes et al. | |
| 6,452,514 B1 | 9/2002 | Philipp | 341/33 |

FOREIGN PATENT DOCUMENTS

| | | | | |
|---|---|---|---|---|
| DE | 3923595 | 12/1990 | | G01N/27/14 |
| DE | 19708053 | 9/1998 | | G01N/27/06 |
| GB | 668196 | 3/1952 | | |
| GB | 2159956 | 12/1985 | | G01N/7/02 |
| WO | WO8504718 | 10/1985 | | G01N/27/22 |

OTHER PUBLICATIONS

"Silicon Sensors," S. Middlehoek and S.A. Audet, Delft University Press, 1994, pp. 230–265.

"The Long–Term Reliability of a Switched–Capacitor Relative Humidity Sensor System," M.A.S. Jaafar et al., Sensors and Materials 3, 2 (1991), pp. 111–125.

* cited by examiner

Primary Examiner—Dean A. Reichard
Assistant Examiner—T. Ha Nguyen
(74) Attorney, Agent, or Firm—Donald S. Dowden; Cooper & Dunham LLP

(57) ABSTRACT

A sensor, in particular a humidity sensor, comprises a measuring layer (4), the dielectric properties of which depend on a parameter to be measured, e.g. of the humidity of the environmental air. Electrodes (2, 3) are arranged on a substrate (1) side by side for capacitively measuring the measuring layer (1). A protective layer (8) of a non-oxidizing material, in particular a layer of silicon oxide or gold, is arranged between the electrodes (2, 3) and the measuring layer (4). This layer prevents an oxidation of the electrodes (2, 3) and increases the live time and reliability of the sensor.

20 Claims, 2 Drawing Sheets

CAPACITIVE SENSOR

CROSS REFERENCE TO RELATED APPLICATIONS

This application claims the priority of Swiss patent application 2251/99, filed Dec. 8, 1999, the disclosure of which is incorporated herein by reference in its entirety.

BACKGROUND

The invention relates to a sensor according to the preamble of claim 1 as well as a method for producing such a sensor.

STATE OF THE ART

Typical examples for sensors of this type are humidity sensors. These comprise a polymer or ceramic layer, which lies on two interdigital electrodes. The dielectric constant of the polymer layer and therefore also the electric capacity between the two electrodes depends on the humidity content of the environmental air. Hence, the humidity content can be determined by means of a capacitive measurement.

In practice it is found, however, that sensors of this type are subject to aging. The signal of a constant parameter to be measured changes over time. This makes later recalibrations necessary and can make the sensors useless.

BRIEF SUMMARY OF THE INVENTION

Hence, it is an object of the invention to provide a sensor of the type mentioned initially that is subject as little as possible to the aging processes mentioned above.

This object is achieved by the sensor of claim 1.

According to the invention, a protective layer of a gas proof, non-oxidizing material is arranged between the electrodes and the measuring layer. As it is found, this reduces or even prevents aging processes. It is assumed that the protective layer prevents an oxidation of the electrodes.

The invention is especially effective with electrodes of aluminum or electrodes of another material that is oxidized easily, such as copper, titanium, tungsten or polysilicon. Aluminum is, however, especially preferred because it is suited for production on semiconductor chips using lithographic methods.

The protective layer can consist of a noble metal, such as gold, or a non-oxidizing dielectric, in particular silicon oxide or silicon nitride. Noble metals and in particular gold have the advantage that they are suited for selective galvanic deposition on the electrodes. For a particularly good sealing, combined layers of gold and a nonoxidizing dielectric deposited thereon are possible as well.

In a preferred embodiment the sensor consists of a semiconductor chip in which an opening is arranged. The opening is spanned by a membrane and the measuring layer is arranged at the membrane. This allows a better control of the temperature of the measuring layer, in particular if a suited heating element is provided. Preferably, the measuring layer is arranged at the inner side of the membrane such that the outer side and therefore the circuit side of the semiconductor chip can be separated from the medium to be measured.

The invention is especially suited for humidity sensors, gas sensors, etc.

BRIEF DESCRIPTION OF THE DRAWINGS

Further embodiments, advantages and applications of the invention result from the dependent claims and the now following description by reference to the figures, which show:

DETAILED DESCRIPTION OF THE INVENTION

Figure 1:
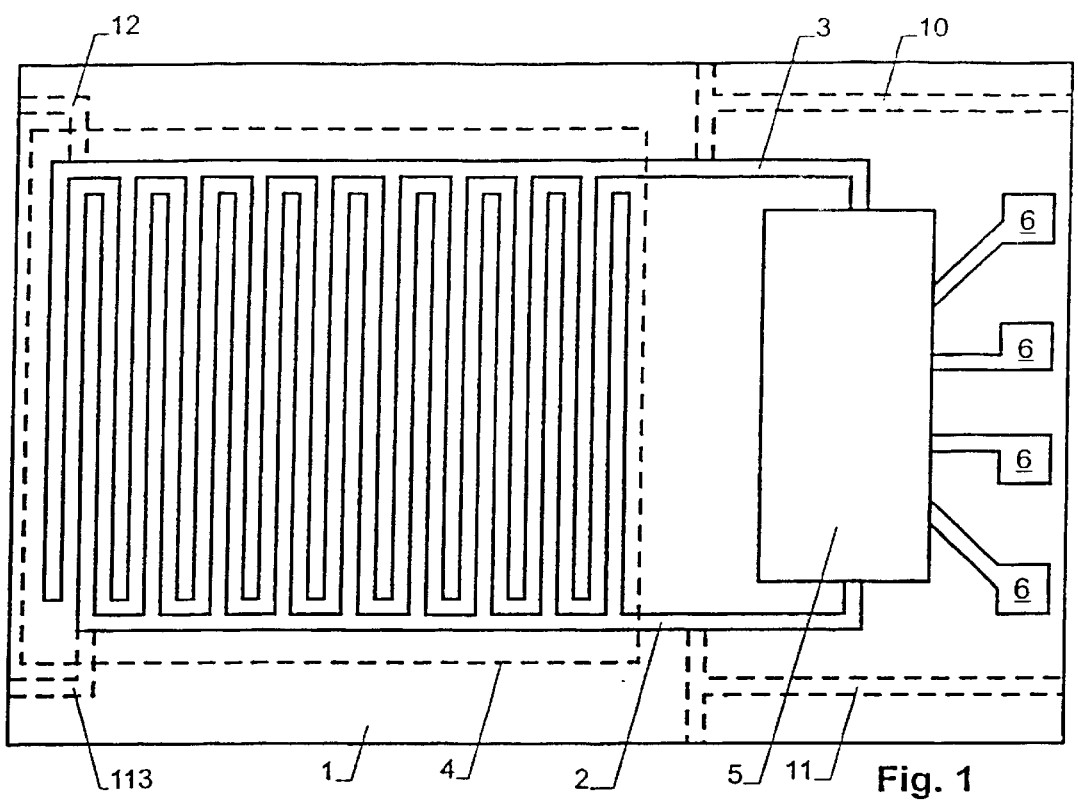
FIG. 1 a top view of a sensor with measuring layer shown in dashed lines.

The sensor shown in FIG. 1 is designed as a humidity sensor. It comprises a semiconductor chip 1 as a substrate, onto which two interdigital electrodes 2, 3 are arranged in known manner. They form a measuring area, on which a measuring layer 4 is arranged, which consists of a polymer or ceramics in the present embodiment. An measuring circuit 5 integrated on the semiconductor chip 1 is used for measuring the capacity between the electrodes 2, 3. For connecting the sensor, suited contact pads 6 are provided.

The electrodes 2, 3 consist preferably of aluminum because this material can be applied to the semiconductor chip 1 with known processes. It is, however, also possible to use electrodes of copper, polysilicon, tungsten or titanium.

The measuring layer 4 is designed such that it absorbs humidity from the environment. Its dielectric constant, and hence the capacity between the electrodes 2, 3, therefore depends on the environmental humidity. The measurement of the capacity therefore allows to measure the humidity of the environment.

Figure 2:
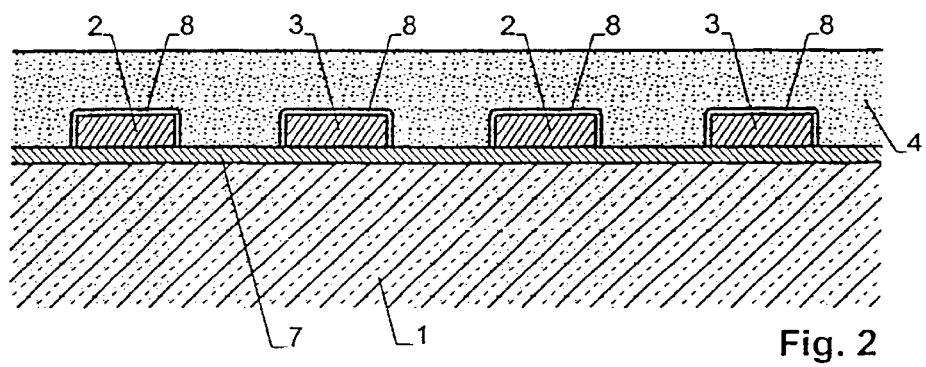
FIG. 2 a sectional view of a first embodiment of the sensor of FIG. 1.

FIG. 2 shows the design of a first embodiment of the invention in detail. As can be seen here, the electrodes 2, 3 lie on a isolating layer 7, which consists of silicon oxide and isolates the electrodes electrically from the semiconductor chip 1. Furthermore, each electrode 2, 3 is individually surrounded by a protective layer 8, which consists in the present case of gold or another noble metal that does not (or only much more slowly than the electrodes) oxidize and is gas proof, i.e. not permeable for oxygen.

The protective layer 8 separates the electrodes 2, 3 from the measuring layer 4 and prevents their oxidation. This avoids aging processes.

During production of the sensor, the electrodes 2, 3 are first applied to the isolating layer 7. Then the electrodes 2, 3 are galvanically coated with gold or another noble metal. For this purpose, a whole semiconductor wafer with several semiconductor chips is brought into a suited galvanic bath. The electrodes are biased electrically in order to form the protective layer 8 at their surface: For this purpose the electrodes 2, 3 of all semiconductor chips 1 can be electrically interconnected by means of suited auxiliary connections 10–13. These auxiliary connections are disconnected when sawing the semiconductor chips 1 apart.

Instead of a protective layer 8' of a noble metal, or in addition to such a protective layer, a protective layer 8' of a tight, non-oxidizing dielectric can be provided, e.g. of silicon oxide or silicon nitride. Silicon oxide is preferred because it is very tight and can furthermore be applied easily using known methods.

Figure 3:
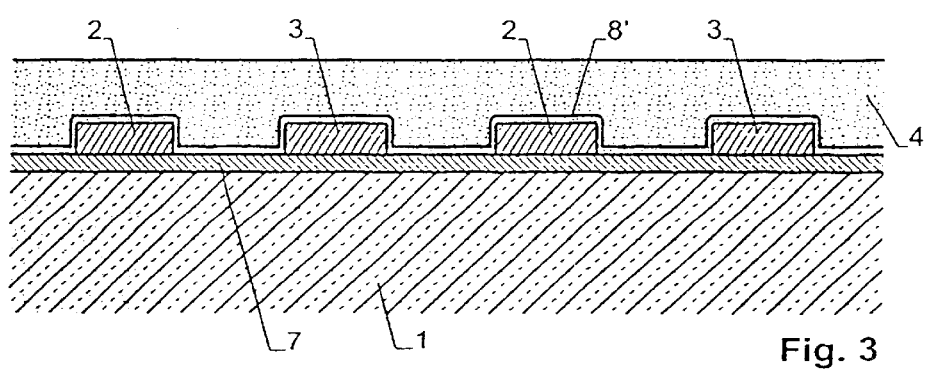
FIG. 3 a sectional view of a second embodiment of the sensor of FIG. 1.

A typical thickness of the protective layer 8, 8' lies between 1 and 100 nm. As shown by FIG. 3, the whole measuring area, i.e. also the areas between the electrodes 2, 3 can be covered by the protective layer if a non-conducting protective layer is used.

Figure 4:
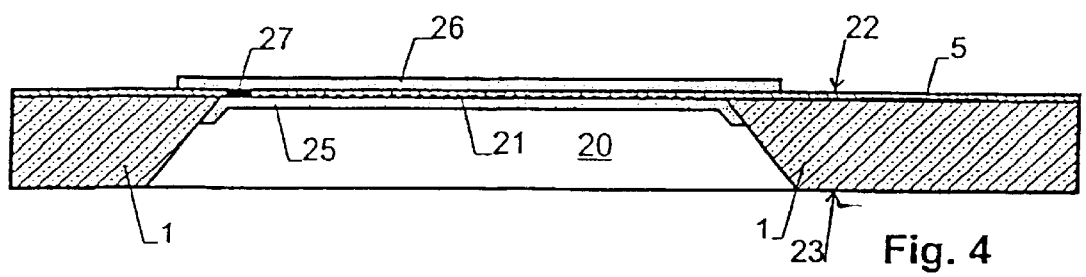
FIG. 4 a sectional view of an embodiment of the sensor with a measuring layer arranged at the bottom, and FIG. 5 a detail of FIG. 4.
Figure 5:
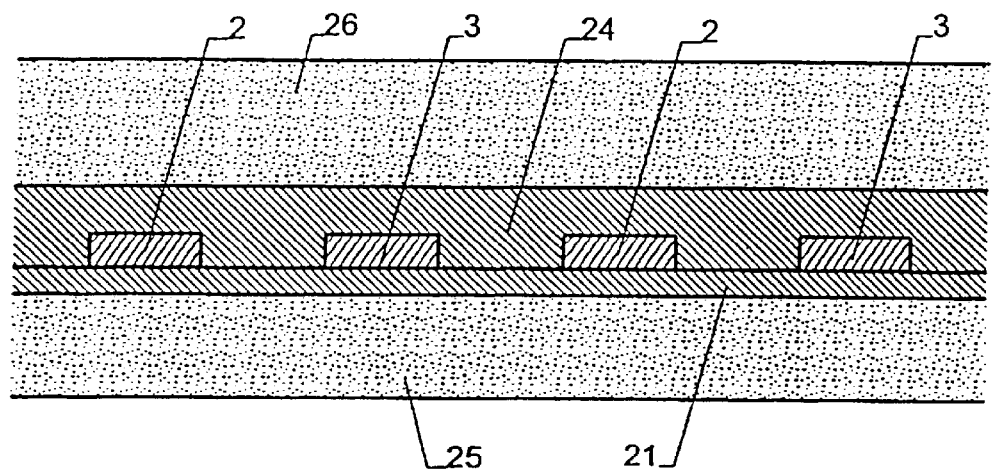

A further embodiment of the invention is shown in FIG. 4 and 5. Here, an opening 20 has been made in semiconductor chip 1. This opening 20 is spanned by a membrane 21, which e.g. consists of silicon oxide. Such an arrangement can be produced by fist applying a silicone oxide to the top side 22 of the semiconductor chip 1 and then creating the opening 20 from the bottom side 23 by anisotropic etching.

The electrodes 2, 3 are arranged on the membrane 21. They are covered by a further, electrically isolating layer 24, e.g. of silicon oxide. A first polymer layer 25 (or a layer of another suited material) lies at the bottom side of the membrane 21. A second polymer layer 26 lies on top of the isolating layer 24. The two polymer layers 25, 26 substantially have the same thermal expansion properties. In this manner, mechanical tensions in the membrane 21 can be avoided.

The polymer layer 25 as well as the polymer layer 26 can be used as measuring layers. Using the lower polymer layer 25 as a measuring layer is, however, preferred. In that case the membrane 21, if it covers the opening 20 completely, can serve as a barrier between the medium to be measured in opening 20 and the top side 22 of the semiconductor chip 1. In this manner the integrated circuit 5 on the top side 22 of the semiconductor chip 1 is protected from the influence of the medium to be measured.

The arrangement of FIGS. 4 and 5 has the advantage that the temperature of the measuring layer can be regulated quickly and easily because it is thermally isolated from the semiconductor chip. For this purpose, a heating element 27 is provided, which is only shown schematically in FIG. 4, and which extends preferably, if possible, over the whole membrane.

In practice it has been found that the sensors shown here provide measuring results that are stable over a long period of time. This is in particular attributed to the protective layer 8, 8' and 21, respectively, because it prevents the electrodes 2, 3 from oxidizing.

The concept shown here is not only suited for humidity sensors, but e.g. also for other types of gas sensors, such as alcohol or $CO_2$ sensors.

While presently preferred embodiments of the invention are described in the present application, it is to be understood that the invention is not limited thereto and can be carried out in other manner within the scope of the following claims.

While there are shown and described presently preferred embodiments of the invention, it is to be distinctly understood that the invention is not limited thereto but may be otherwise practiced within the scope of the following claims.

What is claimed is:

1. A sensor comprising
  a measuring layer having dielectric properties that depend on a parameter to be measured,
  a semiconductor chip,
  interdigital electrodes lying on the semiconductor chip side by side for capacitively measuring the measuring layer, and
  a protective layer of gas proof, non-oxidizing material arranged between the electrodes and the measuring layer.

2. The sensor of claim 1 wherein the protective layer has a thickness between 1 and 100 nm.

3. The sensor of claim 1 wherein the interdigital electrodes are of aluminum.

4. The sensor of claim 1 wherein the interdigital electrodes are of copper, titanium, tungsten or polysilicon.

5. The sensor of claim 1 wherein the protective layer consists at least partially of a noble metal.

6. The sensor of claim 5 wherein the protective layer consists of a first layer of a noble metal and a second layer of a non-oxidizing dielectric.

7. The sensor of claim 1 wherein the measuring layer comprises a polymer.

8. The sensor of claim 1 wherein it is a humidity sensor and that the dielectric constant of the measuring layer depends on the environmental humidity.

9. The sensor of claim 5 wherein said noble metal is gold.

10. The sensor of claim 1 wherein the protective layer consists at least partially of a non-oxidizing dielectric.

11. The sensor of claim 10 wherein the non-oxidizing dielectric is silicone oxide.

12. A sensor comprising
  a measuring layer having dielectric properties that depend on a parameter to be measured,
  a semiconductor chip,
  interdigital electrodes lying on the semiconductor chip side by side for capacitively measuring the measuring layer, and
  a protective layer of gas proof, non-oxidizing material arranged between the electrodes and the measuring layer,
  wherein an opening spanned by a membrane is arranged in the semiconductor chip, wherein the interdigital electrodes are arranged on or within the membrane and the measuring layer is arranged at the membrane.

13. The sensor of claim 12 wherein a compensation layer is arranged on a side of the membrane opposite to the measuring layer, wherein the compensation layer has substantially the same thermal expansion properties as the measuring layer.

14. The sensor of claim 12 wherein the membrane consists of silicon oxide or silicon nitride.

15. The sensor of claim 12 wherein the measuring layer is located on an inner side of the membrane facing the opening and the membrane forms the protective layer.

16. The sensor of claim 13 wherein the compensation layer is of the same material as the measuring layer and has substantially the same thickness as the measuring layer.

17. The sensor of claim 15 further comprising a circuit arranged on said semiconductor chip, wherein the membrane and the circuit are arranged on a first side of the semiconductor chip and wherein the membrane forms a barrier between the first side and the opening.

18. The sensor of claim 12 further comprising a heating element arranged on the membrane.

19. A method for producing a sensor comprising the steps of
  applying interdigital electrodes to a semiconductor chip,
  applying a protective layer of gas proof, non-oxidizing material layer on the interdigital electrodes, and
  applying a measuring layer, having dielectric properties that depend on a parameter to be measured, over the protective layer.

20. The method of claim 19 wherein the protective layer is applied on the interdigital electrodes by galvanic deposition of a noble metal.

* * * * *